(12) United States Patent
Eisenmann et al.

(10) Patent No.: US 10,933,250 B2
(45) Date of Patent: Mar. 2, 2021

(54) SKIN TREATMENT APPARATUS AND METHOD

(71) Applicant: Syneron Medical LTD., Yokneam Illit (IL)

(72) Inventors: Shmulik Eisenmann, Pardes Chana-Karkur (IL); Vladimir Goland, Ashdod (IL); Yossef Ori Adanny, Mitzpe Ilan (IL)

(73) Assignee: SYNERON MEDICAL LTD., Yoqneam Illit (IL)

( * ) Notice: Subject to any disclaimer, the term of this patent is extended or adjusted under 35 U.S.C. 154(b) by 584 days.

(21) Appl. No.: 15/293,331

(22) Filed: Oct. 14, 2016

(65) Prior Publication Data
US 2017/0304641 A1    Oct. 26, 2017

Related U.S. Application Data

(60) Provisional application No. 62/326,039, filed on Apr. 22, 2016.

(51) Int. Cl.
*A61N 1/40*    (2006.01)
*A61N 1/04*    (2006.01)
(Continued)

(52) U.S. Cl.
CPC ........... *A61N 1/403* (2013.01); *A61N 1/0476* (2013.01); *A61N 1/06* (2013.01); *A61N 1/328* (2013.01);
(Continued)

(58) Field of Classification Search
CPC . A61N 1/403; A61N 1/06; A61N 1/28; A61N 1/328; A61N 1/0476; A61N 1/046;
(Continued)

(56) References Cited

U.S. PATENT DOCUMENTS

| 5,383,917 A | 1/1995 | Desai et al. |
| 5,620,481 A | 4/1997 | Deasi et al. |

(Continued)

FOREIGN PATENT DOCUMENTS

| WO | WO9600036 | 1/1996 |
| WO | 1999056649 | 11/1999 |

(Continued)

OTHER PUBLICATIONS

Kuphaldt, Tony R, 2001, Design Science License, Lessons in ELectric Circuits, vol. 1—Direct Current (DC), Electrical Safety, Ohm's Law (again!).*

(Continued)

*Primary Examiner* — Linda C Dvorak
*Assistant Examiner* — Annabeth E Rodriguez
(74) *Attorney, Agent, or Firm* — Manelli Selter PLLC; Edward Stemberger

(57) ABSTRACT

Disclosed is a system and a method for aesthetic skin treatment. The system includes an array of RF electrodes assembled on a flexible or rigid substrate. A plurality of RF voltage generators configured to address individually each of the RF electrodes of the array and supply to each pair of RF electrodes RF voltage. The amplitude of the RF voltage applied to inner pair of RF electrodes is lower than the RF voltage applied to outer pair of RF electrodes.

31 Claims, 9 Drawing Sheets

(51) Int. Cl.
*A61N 1/32* (2006.01)
*A61N 1/06* (2006.01)
*A61B 5/053* (2021.01)
*A61B 5/0531* (2021.01)
*A61B 5/0537* (2021.01)
*A61B 5/00* (2006.01)

(52) U.S. Cl.
CPC ........... *A61B 5/0531* (2013.01); *A61B 5/0537* (2013.01); *A61B 5/441* (2013.01)

(58) Field of Classification Search
CPC ..... A61B 5/0541; A61B 5/0537; A61B 5/441; A61B 18/1206; A61B 18/14; A61B 2018/0016; A61B 2018/0047; A61B 2018/1273; A61B 2018/1467; A61B 5/0531
USPC .................................................. 607/101, 102
See application file for complete search history.

(56) References Cited

U.S. PATENT DOCUMENTS

| | | |
|---|---|---|
| 5,868,736 A | 2/1999 | Swanson et al. |
| 5,931,835 A | 8/1999 | Mackey |
| 6,228,078 B1 | 5/2001 | Eggers et al. |
| 6,283,987 B1 | 9/2001 | Laird et al. |
| 6,635,056 B2 | 10/2003 | Kadhiresan et al. |
| 6,730,078 B2 | 5/2004 | Simpson et al. |
| 6,746,447 B2 | 6/2004 | Davison et al. |
| 7,151,964 B2 | 12/2006 | Desai et al. |
| 8,133,216 B2 * | 3/2012 | Knopp ................... A61B 18/14 606/32 |
| 8,206,381 B2 * | 6/2012 | Lischinsky ........ A61B 18/1206 606/34 |
| 8,652,130 B2 | 2/2014 | Kreindel |
| 8,728,071 B2 | 5/2014 | Lischinsky et al. |
| 2008/0091184 A1 * | 4/2008 | Knopp ................... A61B 18/14 606/31 |
| 2013/0226269 A1 * | 8/2013 | Eckhouse ........... A61N 1/0496 607/88 |
| 2013/0238062 A1 * | 9/2013 | Ron Edoute ............. A61N 7/02 607/102 |
| 2017/0189703 A1 * | 7/2017 | Lei ........................... A61N 1/06 |
| 2018/0000533 A1 * | 1/2018 | Boll .................. A61B 18/1206 |

FOREIGN PATENT DOCUMENTS

| | | |
|---|---|---|
| WO | 2007099460 A2 | 9/2007 |
| WO | 2012052986 A2 | 4/2012 |
| WO | WO-2016012147 A1 * | 1/2016 ......... A61B 18/1206 |

OTHER PUBLICATIONS

Luna, Dynamic IMpedance Model of the Skin-Electrode Interface for Transcutaneous Electrical Stimulation, May, 5, 2015, PLOS, vol. 10, Issue 5, pp. 1-15 (Year: 2015).*

* cited by examiner

SKIN TREATMENT APPARATUS AND METHOD

FIELD OF TECHNOLOGY

The apparatus and method are related to methods and apparatuses for cosmetic skin treatment and in particular to skin rejuvenation and skin tightening procedures that reduce the appearance of wrinkles that occurs in aged skin.

BACKGROUND

Radiofrequency (RF) energy treatment is a technology widely used for many non-invasive cosmetic and aesthetic skin treatments. Radio Frequency (RF) energy is applied or coupled to skin by an applicator that includes at least one electrode and frequently by two or more electrodes. Application to skin of RF energy heats the segment of skin or tissue located between the electrodes. Such skin heat treatment is a popular non-invasive treatment method for skin rejuvenation, skin tightening, vessel shrinkage, wrinkles reduction, collagen rejuvenation, acne treatment and other skin treatment procedures. Application of RF energy heats dermis and subcutaneous tissue while minimizing heating of the epidermis and consequently reducing damage to the superficial skin layers. The observed tissue contraction immediately after the therapy is believed to result from modifications in the collagen structure due to temperature increase in the dermal layer. Subsequent formation of new collagen fibers then ensures a beneficial for external appearance skin changes.

Most of the skin treatments could be performed only when the skin reaches an optimal treatment temperature and at optimal depth below the skin surface. In reaching the optimal treatment temperature and depth, several factors are considered, such as location of the skin segment, energy coupled to the skin, electrode size and number of electrodes.

Skin treatment applicators and systems in which multiple RF electrodes are used, either on a common substrate or coordinated in another way are known. For skin treatment each RF electrode is supplied with RF energy and brought in contact with the skin. The electrodes may be arranged in different configurations and patterns to allow for a specific use of RF energy according to the application desired in each treatment.

The following U.S. Pat. Nos. 5,383,917, 5,620,481, 5,868,736, 5,931,835, 6,228,078, 6,283,987, 6,635,056, 6,730,078, 6,746,447, 7,151,964, 8,206,381, 8,652,130, 8,728,071 and Patent Cooperation Treaty Publications WO1996/000036, and WO1999/056649 may be of interest.

Definitions

Skin rejuvenation is a general term for skin treatment that includes improving skin texture, reduction of fine facial wrinkles, and removal of vascular and pigmented lesions.

In the context of the present disclosure the terms "skin" and "tissue" are used interchangeably and have the same meaning. The terms include the outer skin layers such as stratum corneum, dermis, epidermis, and the deeper subcutaneous layers such as adipose tissue.

The term "bipolar electrodes" as used in the present disclosure means that the RF induced current passes between two usually identical electrodes located a short distance apart from each other. The electrodes are applied to the target volume of skin/tissue and the propagation of the current is limited predominantly to the volume of skin/tissue between the electrodes.

The term "RMS" as used in the present disclosure stands for "Root-Mean-Squared", which is the "amount of AC power that produces the same heating effect as an equivalent DC power". The RMS value is the square root of the mean (average) value of the squared function of the instantaneous values. The symbols used for defining an RMS value are VRMS or IRMS. Generally, the term RMS, only refers to time-varying sinusoidal voltages.

The term "computer" as used in the present disclosure means a device capable of receiving data or information, processing it, and delivering the data processing results to another device. As such, a computer may include, as non-limiting examples, a personal computer, a PDA computer, a mobile telephone, and similar devices. Typically, a computer as defined herein would have a display but, other forms of user feedback, prompting and user interface may also be used such a sound, voice detection, brail screens, or the like.

As used herein, the term "subject" refers to any human or animal subject, as well as synthetic objects.

As used herein, the term "active group of electrodes" or "active electrodes" means a pair or a group of electrodes to which RF voltage is supplied. The number of "active electrodes" in a group could be variable and adapted to a particular treatment.

As used herein, the terms "outer electrodes" and "inner electrodes" are used to indicate location of RF electrodes within an array of electrodes. The outer electrodes are flanking the inner electrodes and the inner electrodes are nested between the outer electrodes.

As used herein, the terms "optical radiation sources" and "optical radiation emitters" have the same meaning and refer to any source or emitter of visible or non-visible optical radiation.

SUMMARY

Application to skin of RF energy heats the segment of skin or tissue located between the RF electrodes and affects some of the skin properties. The current document discloses a method and apparatus for delivering RF energy to an area of skin to heat it. The method and apparatus is facilitated by an applicator including a plurality of RF electrodes configured to contact the skin. The RF electrodes are arranged into an array with at least a pair of outer RF electrodes flanking at least an inner RF electrodes nested between them. A plurality of synchronized but independently operated RF voltage generators apply to each pair of RF electrodes RF voltage. Another option is to use a single RF generator that is connected to the electrode pairs via a voltage divider. Either one of these setups facilitates an amplitude of the RF voltage applied to inner pair of RF electrodes which is different than the RF voltage applied to outer pair or pairs of RF electrodes.

The electric current streamlines produced by the RF voltage applied to the outer RF electrodes penetrate into the skin deeper than the electric current streamlines produced by the RF voltage applied to the inner RF electrodes. The electric current streamlines produced by the RF voltage applied to the outer RF electrodes limit penetration of the current stream lines produced by the inner RF electrodes and the electric current streamlines produced by the RF voltage applied to the outer and inner electrodes are heating a common skin volume located about the middle of the distance between the inner RF electrodes. The common skin volume is located at least 1 micron below the skin surface and extends at least the length of the RF electrodes.

The RF electrodes are arranged into an array that could be a linear array, a plurality of staggered linear arrays shifted relative to each other and a two dimensional array of RF electrodes. The arrays are arranged on a substrate that could be a rigid or a flexible substrate. The flexible substrate could be attached to the relief of a treated skin area.

In addition to the RF voltage generators and applicator the system includes a vacuum pump is configured to provide vacuum to the flexible substrate such as to attach the substrate to the relief of a treated skin area and a control unit, which could be a personal computer having a processor circuit configured to control each of the plurality of RF voltage generator, RF energy to RF electrodes supply sequence, operation of the vacuum pump and other processes.

The control unit sets the amplitude of the RF voltage supplied to each electrode pair according to expression:

$$V_i \sim \{(1/\pi\sigma)[c_i \ln(d/4) + \Sigma c_j \ln|x_j - x_i|]\}$$

The system further includes a scanning unit configured to translate a linear array across the skin.

The system also includes an arrangement to measure different skin parameters. This could include skin and fat thickness and electric conductivity and or permittivity.

BRIEF DESCRIPTION OF THE DRAWINGS

In order to understand the apparatus and method and to see how it may be carried out in practice, examples will now be described, by way of non-limiting example only, with reference to the accompanying drawings, in which.

DETAILED DESCRIPTION

Application to skin of RF energy heats the segment of skin or tissue located between the RF electrodes. It is suggested that electrical current induced by application to skin of RF energy and in particular by bi-polar devices flow along the lowest impedance path between electrodes which is almost parallel to the skin surface. Depending on RF energy supplied to the RF electrodes, it could affect the upper closest to the surface of the skin or deeper skin layers. In order to treat an additional skin segment or change the depth of the treatment the RF electrodes should be repositioned, the RF energy supplied to the electrodes should be changed and in some cases the distance between the electrodes should be changed.

Figure 1A:
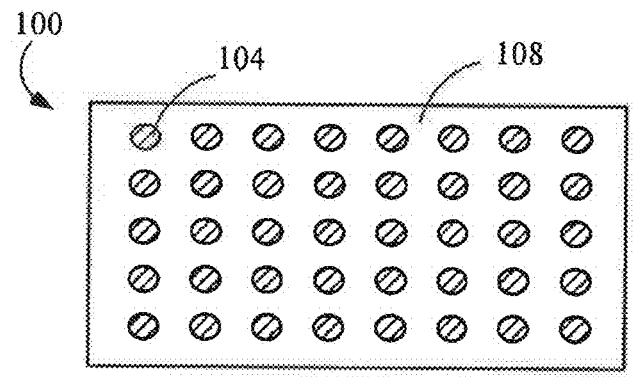
FIGS. 1A-1C are an examples of an existing substrate including a plurality of RF electrodes.
Figure 1B:
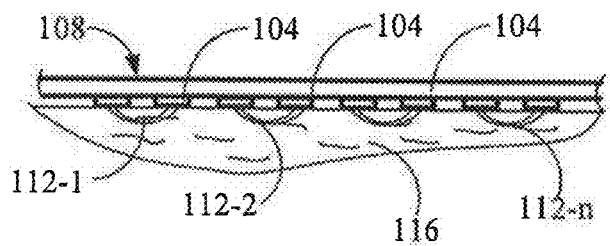
Figure 1C:
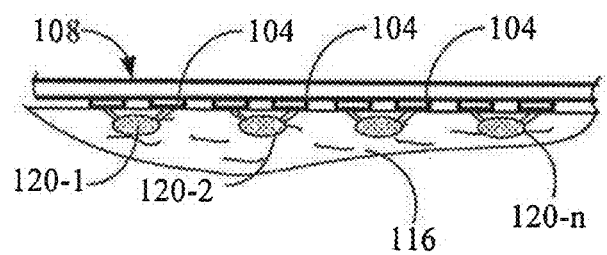

European patent EP 2 627 400 (WO2012/052986) to the same assignee discloses a device 100 (FIG. 1) for heating the skin of a subject. The device includes a plurality of RF electrodes 104 arranged in a two dimensional array on a substrate 108. The RF electrodes are applied to a treated subject's skin at respective points. The RF voltage may be supplied individually to each of the electrodes, to a pair or electrodes, to a group of electrodes, and to all electrodes of the device according to a predetermined experimentally established protocol. Numeral 112 marks electric current streamlines generated in skin 116 between pairs of electrodes 104 by the applied RF voltage. Numeral 120 marks skin volumes heated by the electric current generated in skin 116 between electrodes 104 by the applied RF voltage.

Uniform spacing between the electrodes 104 enables treatment of all skin segments, actually skin volumes 120, located below the skin segments surface, to which the substrate with electrodes 104 is applied at the same skin treatment depth. For treatment of skin layers located at other skin depths, substrates with different spacing or distance between the electrodes 104 may be used.

Use of the device necessitates storage of a variety of substrates populated by a plurality of electrodes arranged at different distance or spacing from each other. The drawback of the device is evident.

Figure 2:
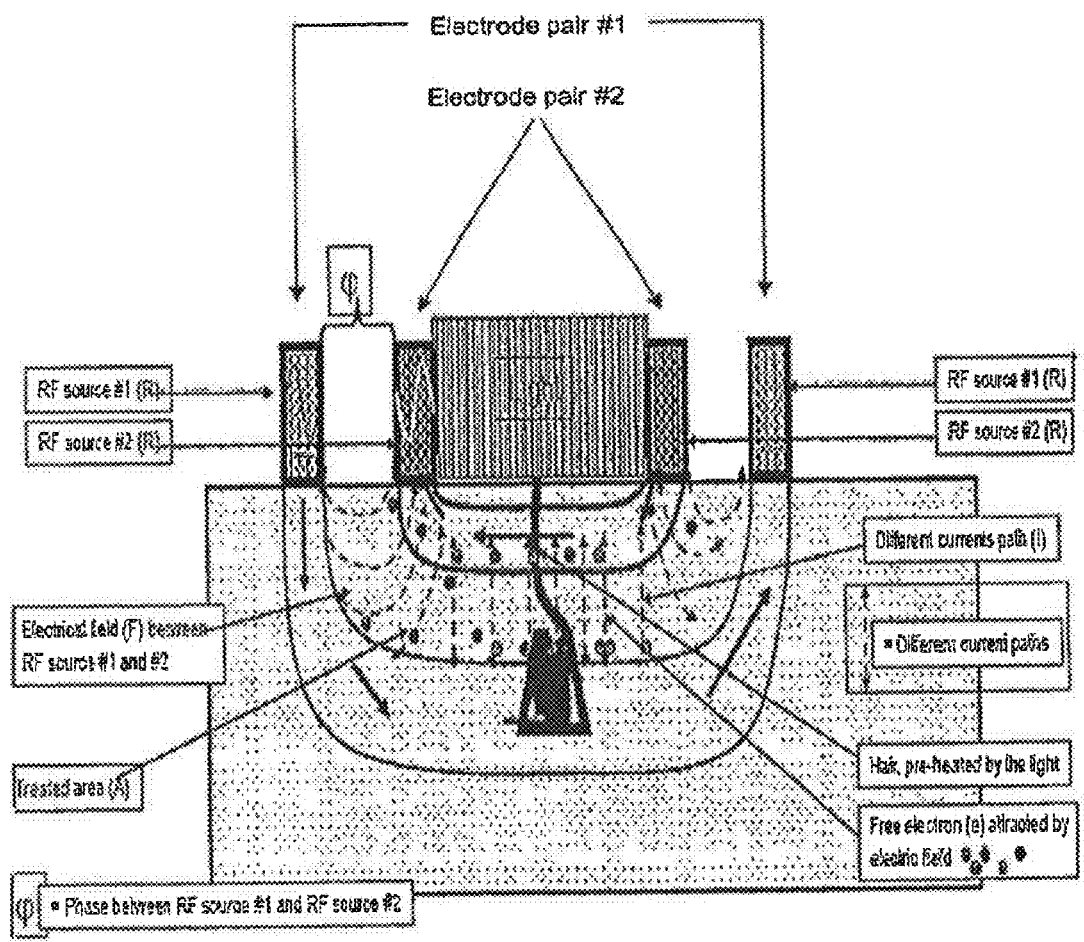
FIG. 2 is an example of another existing substrate including a plurality of RF electrodes.

Patent Cooperation Treaty publication WO2007/099460 to Lischinsky discloses a substrate with RF electrodes connected in pairs, for example two pairs, labeled RF1 and RF2 (FIG. 2). The distance between the electrodes is different for each pair. A phase controlled RF energy delivered to each pair of RF electrodes. The phase controlled RF voltage generates different and adjustable electrical fields within the target site. The electrical fields are capable of manipulating electrons within the target site, thereby generating selective regions of elevated temperature. Control of the phase shift allows operation of different electrode pairs and reach different skin treatment depth and percentage of tissue to be damaged. The phase shift is typically used for producing electric currents flowing simultaneously between different electrodes, the inter-electrode directions being different. For example, the focal damage regions may be substantially columnar and perpendicular to the surface of the skin being treated. The columns may begin at or below the surface of the skin and extend to some depth below the surface.

The present disclosure supports adjustment of RF voltage amplitudes supplied to different electrodes to provide a predefined RMS (Root-Mean-Squared) of electric currents flowing through each electrode. Particularly, the method is equalizing the currents flowing through different electrodes to avoid getting excessive hotspots in the vicinity of some of the electrodes. The method also supports the RF voltage control to channel specific groups of electrodes and formation of desired electric field streamlines. The channeling of RF voltage to specific groups of electrodes facilitates generation of a desired heat deposition pattern.

The authors of current application want to emphasize the difference between a phased-controlled array of RF electrodes and amplitude-controlled array of RF electrodes. Usually for aesthetic (cosmetic) and medical application RF frequencies in the 0.3-300 MHz range are used. These frequencies correspond to wavelengths of 1-1000 meters. As RF electrodes size and separation are much smaller than these wavelength magnitude, one must understand that the electrodes are not antennas and there is no wave propagation in the sense that different phases will vary spatially creating destructive and constructive interference areas. By this it is meant that it is not possible that in some region between the electrodes interference will be constructive while being destructive in another. Thus, no meaningful focusing of the RF energy can be generated in the region between the electrodes by solely phase-controlling the different pairs of RF electrodes. On the other hand by controlling the amplitude of the RF signal of different RF electrode pairs, one can control the charge on each of the pairs, thus controlling the RF induced current streamlines, allowing for focusing the RF energy in a specific region between the electrodes.

Use of individually driven multiple RF electrodes or emitters of RF energy supports tissue heating in a sequence determined by the RF energy pulses. Continuous supply of RF energy for a period is also supported. Each RF power pulse has a voltage amplitude, which can be different from the amplitude supplied to a neighbor or another RF electrode. The RF voltage amplitude is measured to a common reference point, the natural reference point being electrical ground.

Figure 3:
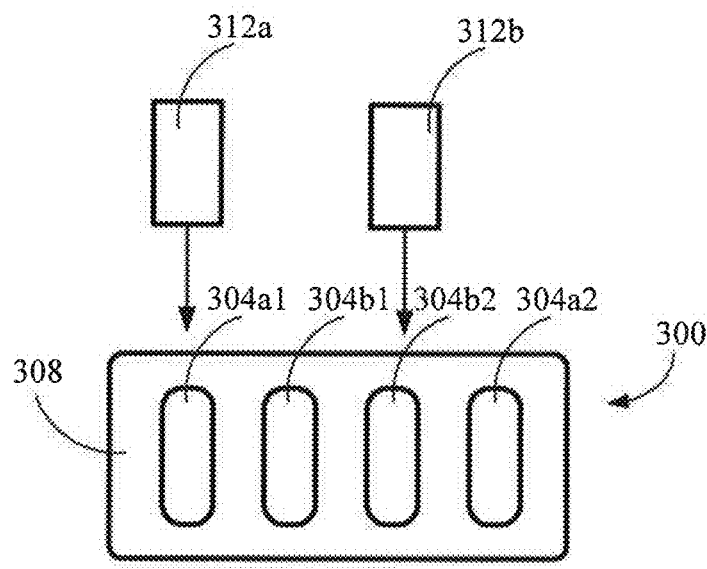
FIG. 3 is a schematic illustration of a substrate with a plurality of electrodes according to an example.

FIG. 3 is a schematic illustration of an applicator with a plurality of electrodes according to an example. Applicator 300 includes RF electrodes or simply electrodes 304 arranged on substrate 308 in an array like structure. Substrate 308 could be a rigid of flexible substrate. RF voltage is supplied to each electrode 304 or pair of electrodes 304a1-304a2, 304b1-304b2 by a plurality of autonomous RF voltage generators 312a and 312b. The operation of the RF voltage generators is synchronized, although each of the RF voltage generators is operating independent from the rest of RF voltage generators. In another example different RF voltage amplitudes could be supplied by a single RF voltage generator through a bank of resistors selected to provide desired RF voltage amplitudes to each pair of electrodes.

Electrodes 304 are communicating with respective RF voltage generators such that the most outer pair of electrodes i.e., electrode pair 304a1-304a2, are receiving or supplied the same RF voltage amplitude by RF voltage generator 312a. RF voltage generators 312b supply different RF voltage amplitude to the inner pair of electrodes i.e., 304b1-304b2. For example, the amplitude of RF voltage supplied to the inner pair of electrodes 304a1-304a2 is lower than the amplitude of RF voltage supplied to outer pair of electrodes 304b1-304b2. The amplitude of the RF voltage supplied to each electrode is calculated according to equation:

$$Vi \sim \{(1/\pi\sigma)[c_i \ln(d/4) + \Sigma c_j \ln|x_j - x_i|]\}$$

Where:
Vi—is the RF voltage amplitude supplied to the i-th electrode, all the voltage values being relative to a common reference point;
σ—is tissue conductivity (S/m);
$c_i/c_j$—is electric current flowing through a particular electrode;
d—is RF electrode width;
$x_i/x_j$—RF electrode center position;
i—index running from 1 to N;
j—index running from 1 to N except for i, i.e. j≠i;
$\Sigma c_j$—the sum of all $c_i$ must equal zero.

RF voltage supplied to different RF electrode pairs is selected to be sufficient to produce the desired effect skin treatment, but not to burn the skin around edges of the RF electrode.

RF voltage amplitude supplied to larger arrays than array 300 could be determined in a similar way. All currents flowing through each electrode have the same amplitude (not the same sign) and the sum of the currents is equal to zero.

Figure 4:
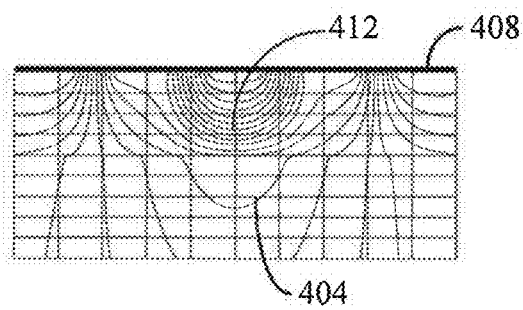
FIG. 4 is a schematic illustration of distribution of electric current streamlines produced by the RF voltage applied to the outer and inner electrodes of the substrate of FIG. 3.
Figure 5:
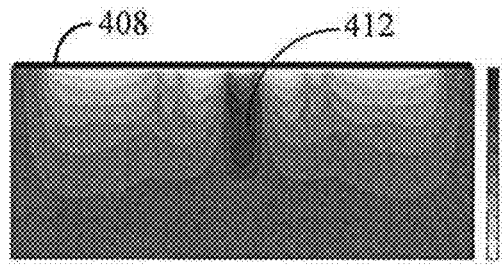
FIG. 5 is an example of temperature distribution in skin caused by application to skin of the substrate of FIG. 3 with the RF voltage applied to the outer and inner electrodes of the substrate.

FIG. 4 illustrates RF voltage induced current streamlines 404 when array 300 is applied to a subject skin surface 408. Current streamlines 404 do not intersect each other. Current streamlines 404 generated by RF voltage supplied to the most inner pair of electrodes 304b1-304b2 have the most shallow penetration depth into the subject skin and are flowing closer to skin surface 408. These currents sum-up in volume 412 with currents induced by the RF voltage supplied to outer electrodes 304a1 and 304a2 and as it is evident from FIG. 5 and confirmed by calculations, the electric current streamlines produced by the RF voltage applied to the outer and inner electrodes are heating a common skin volume 412 located about the middle of the distance between the RF electrodes of array 300. The common skin volume 412 located about the middle of the distance between the electrodes 304 is located at least 1 micron below the skin surface.

Accordingly, by setting/determining the outer RF electrodes in a group of active RF electrodes it is possible to form a target skin volume where the amount of current streamlines 404 produced by the outer RF electrodes and all RF electrodes nested between the outer RF electrodes is most dense. These currents heat the target (common) skin volume located at the desired skin depth and about the middle of the distance between the RF electrodes of array 300, to a desired temperature higher than the surrounding skin is heated.

Figure 6:
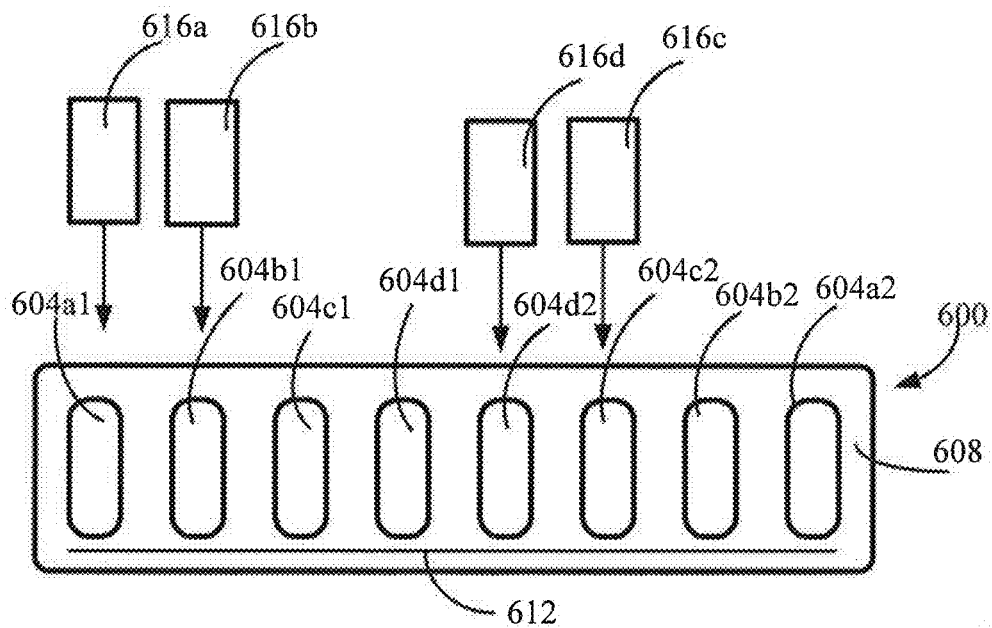
FIG. 6 is a schematic illustration of a substrate with a plurality of electrodes according to another example.

FIG. 6 is a schematic illustration of an applicator 600 including a substrate 608 with a plurality of RF electrodes according to another example. RF electrodes 604 are arranged on substrate 608 in a linear array 612. RF electrodes 604 receive RF voltage from respective RF voltage generators 616 such that the most external electrodes located on one side of the substrate 608 are connected to most external electrodes located on the opposite side of the substrate 608, i.e., electrode 604a1 is paired with electrode 604a2, electrode 604b1 is paired with electrode 604b2 and so on. RF voltage generators 616 supply different RF voltage amplitude to each pair of electrodes. For example, the amplitude of RF voltage supplied to the most inner pair of electrodes 604d1-604d2 is lower than the amplitude of RF voltage supplied to outer (with respect to electrodes 604d1-604d2) pair of electrodes 604c1-604c2. The amplitude of RF voltage supplied to inner (with respect to electrodes 604b1-604b2) pair of electrodes 604c1-604c2 is lower than the amplitude of RF voltage supplied to electrodes 604b1-604b2 and so on. The amplitude of the RF voltage supplied to the most inner pair of electrodes 604d1-604d2 is the lowest amplitude of RF voltage supplied to the array 600 i.e., (Vb>Va>Vc>Vd). In another example different RF voltage amplitudes could be supplied by a single RF voltage generator through a bank of resistors selected to provide desired RF voltage amplitudes to each pair of electrodes.

Figure 7:
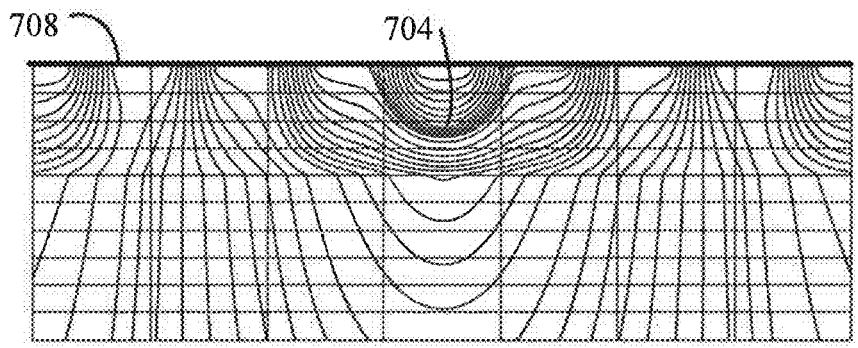
FIG. 7 is a schematic illustration of distribution of electric current streamlines produced by the RF voltage applied to the outer and inner electrodes of the substrate of FIG. 6.

FIG. 7 is a schematic illustration of distribution of electric current streamlines produced by the RF voltage applied to the outer and inner RF electrodes 604 of array 612 of FIG. 6. The figure clear illustrates that there is a common skin volume 704 where the currents induced by RF voltage between different of RF electrode pairs sum-up. This common skin volume 704 is located about the middle of the distance between the RF electrodes of array 612. This common skin volume is located at least 1 micron below the skin surface 708 although the currents induced by RF voltage between different of RF electrode pairs penetrate deeper into the skin 708.

Figure 8:
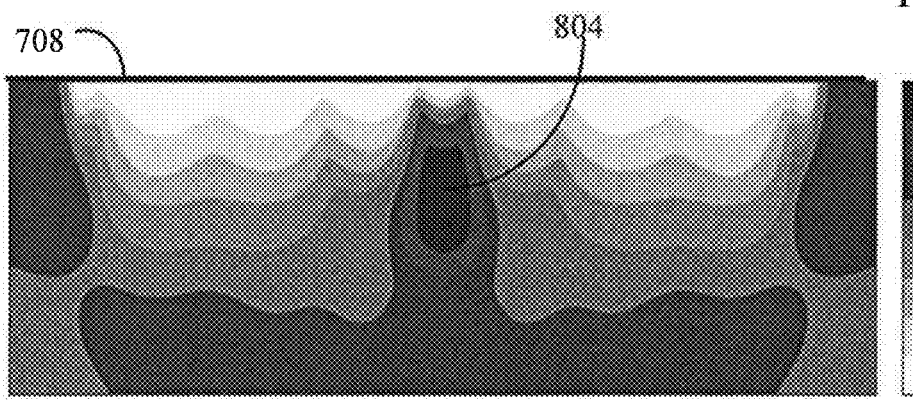
FIG. 8 is an example of temperature distribution in skin caused by application to skin of the substrate of FIG. 6 with the RF voltage applied to the outer and inner electrodes of the substrate.

FIG. 8 is an example of temperature distribution in skin caused by application to skin of the applicator 600 with substrate 608 of FIG. 6 with the RF voltage applied to all (outer and inner) RF electrodes of the substrate 608. The figure illustrates that there is a common skin volume 804 located about the middle of the distance between the RF electrodes of array 600, where the currents induced by RF voltage between different of RF electrode pairs sum-up. This common skin volume is located at least 1 micron below the skin surface 708 and as shown in FIG. 8 extends along the length of electrodes 604. When such array is scanned across the skin it affects a long and deep volume of skin.

Figure 9:
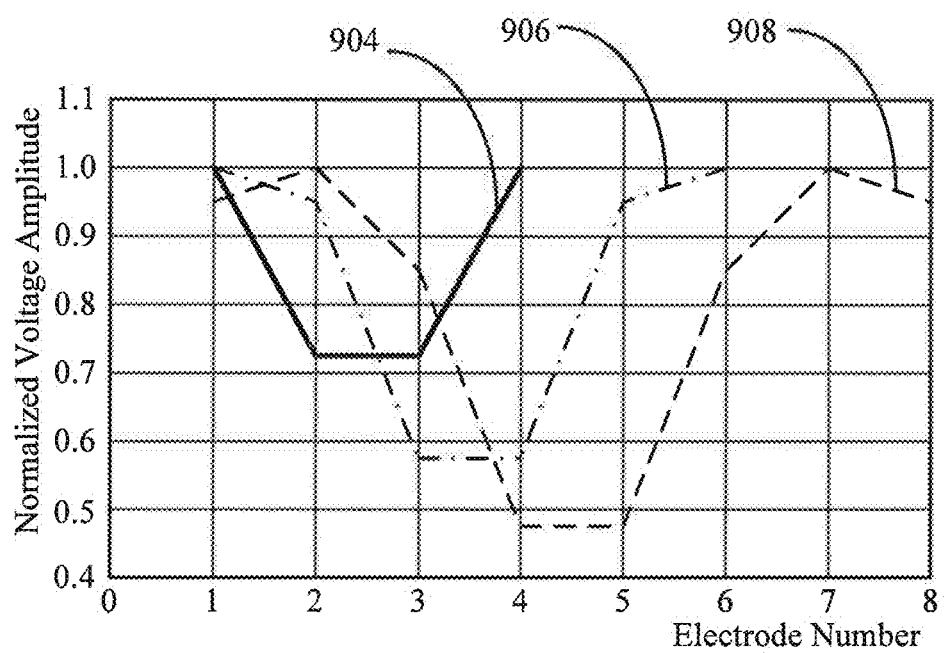
FIG. 9 is a schematic illustration is an example of RF voltage amplitude Vi changes as a function of the RF electrodes array geometry.

As it was indicated above the amplitude of the RF voltage supplied to the most inner pair of electrodes is the lowest RF voltage amplitude supplied to the array of RF electrodes. Generally, the voltage Vi supplied to each pair of electrodes depends on the geometry of the array and number of pair electrodes operated. FIG. 9 is an example of RF voltage Vi amplitude changes as a function of the array geometry. Reference numeral 904 illustrates RF voltage amplitude values for an array of four RF electrodes (two pairs of RF electrodes). Reference numeral 906 illustrates RF voltage amplitude values for an array of six RF electrodes (three pairs of RF electrodes). Reference numeral 908 illustrates RF voltage amplitude values for an array of eight RF electrodes (four pairs of RF electrodes). The RF voltage amplitude supplied to the outer electrodes is higher than the RF voltage amplitude supplied to the inner electrodes, although for larger arrays of RF electrodes a drop down in the RF voltage amplitude e.g., graph 908.

Figure 10A:
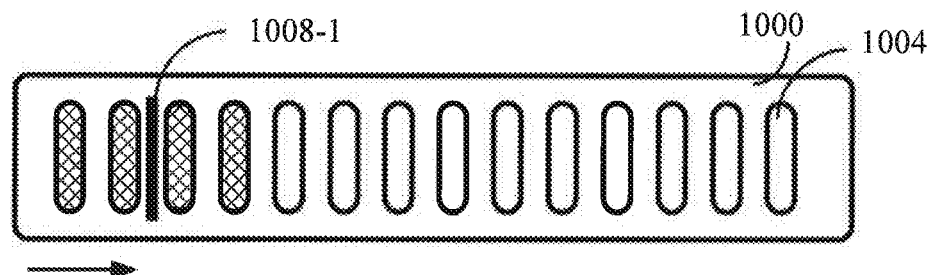
FIGS. 10A-10D are schematic illustrations of electronic scanning of an array of RF electrodes according to an example.
Figure 10B:
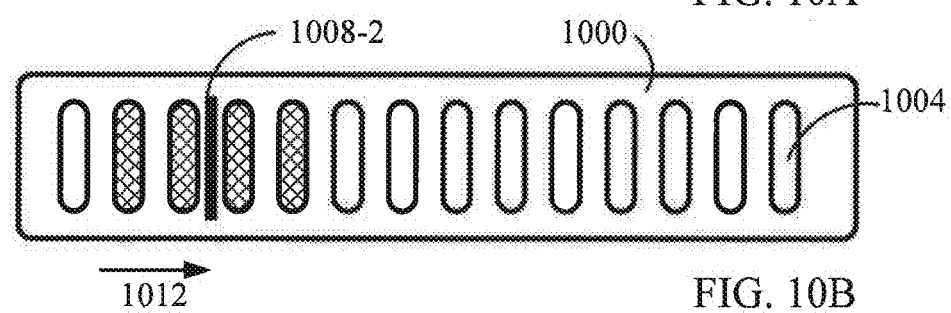
Figure 10C:
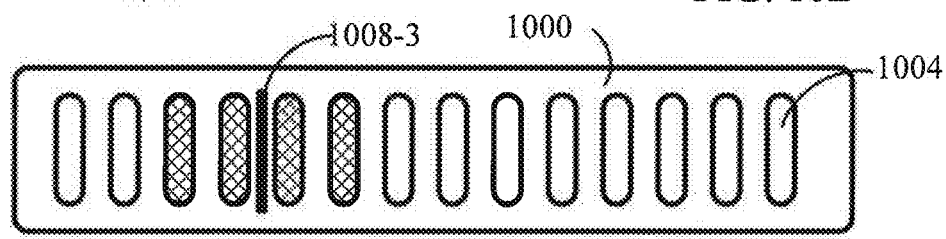
Figure 10D:
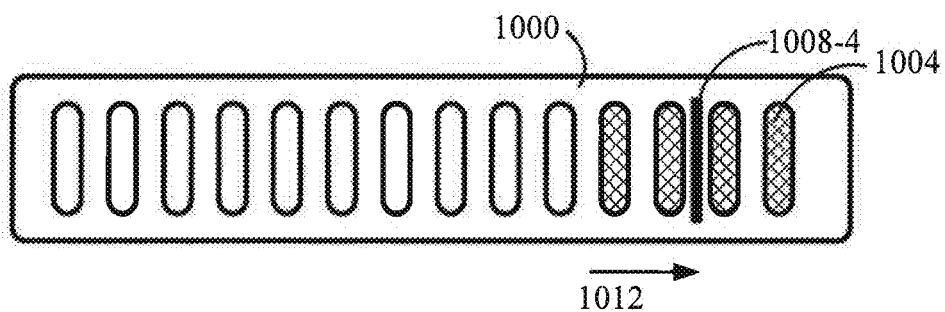

Use of RF electrodes arrays including more than three RF electrodes supports as shown in FIGS. 10A-10D electronic scanning of the treated skin area. Substrate 1000 is populated by a linear array of RF electrodes 1004. Initially (FIG. 10A), first four hatched electrodes are activated and a skin volume 1008-1 located between the most inner RF electrodes is heated to a desired temperature. In FIG. 10B next four hatched RF electrodes are activated and a skin volume 1008-2 located between the most inner RF electrodes 1004 is heated to a desired temperature. Shift between the activated electrodes to heat different skin volumes could continue in the direction indicated by arrow 1012 or in any other order. For example, concurrent operation of different groups of electrodes could also take place.

Figure 11A:
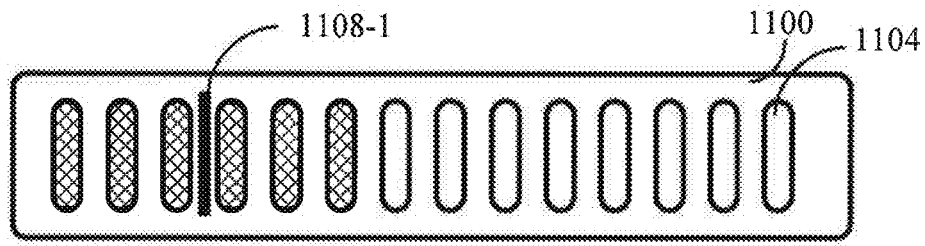
FIGS. 11A-11D are schematic illustrations of electronic scanning of an array of RF electrodes according to another example.
Figure 11B:
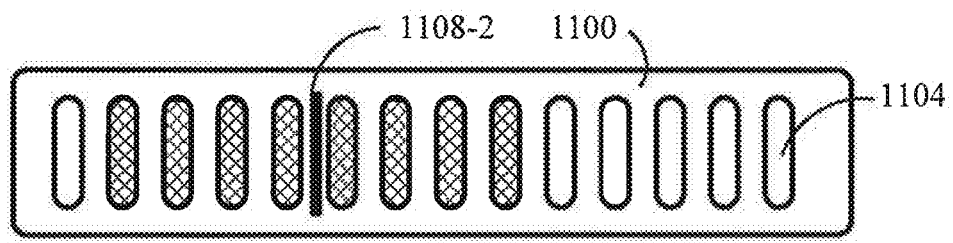
Figure 11C:
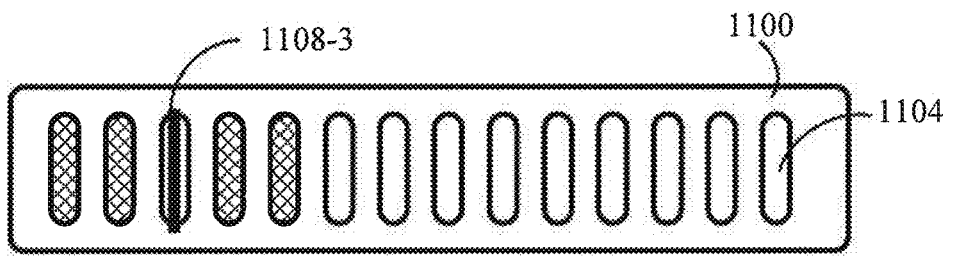
Figure 11D:
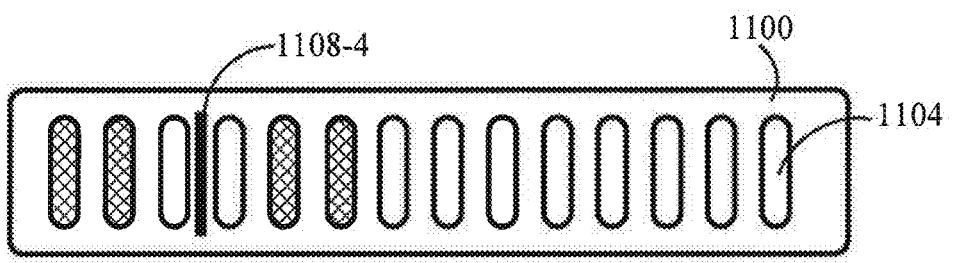

By changing the order and number of active/participating electrodes, array 1100 similar to array 1000, could be used to scan and heat the skin volumes at different depths. In order to perform the skin treatment at a depth greater than in FIG. 10 and heat a volume of skin 1108-1, in FIG. 11A a group of six hatched electrodes 1104 located on substrate 1100 is activated. In order to perform the skin treatment at a depth greater than in FIG. 11A and heat a skin volume 1108-2 in FIG. 11B a group of eight hatched electrodes 1104 is activated. FIG. 11C is another example of activating different RF electrode groups. Each activated group of RF electrodes includes one or more nested in the array 1100 not activated RF electrodes 1104. The method forms heated skin volumes 1108-3 and 1108-4 of different depth. Such method of activation of RF electrode groups supports additional option of varying depth of the skin treatment. In all described above cases the temperature and depth in the skin of the heated volumes could be different. As explained above heated skin volumes are located at least 1 micron below the skin surface and as shown in FIG. 10 and FIG. 11 extend at least the length of electrodes 1004 or 1104.

Figure 12:
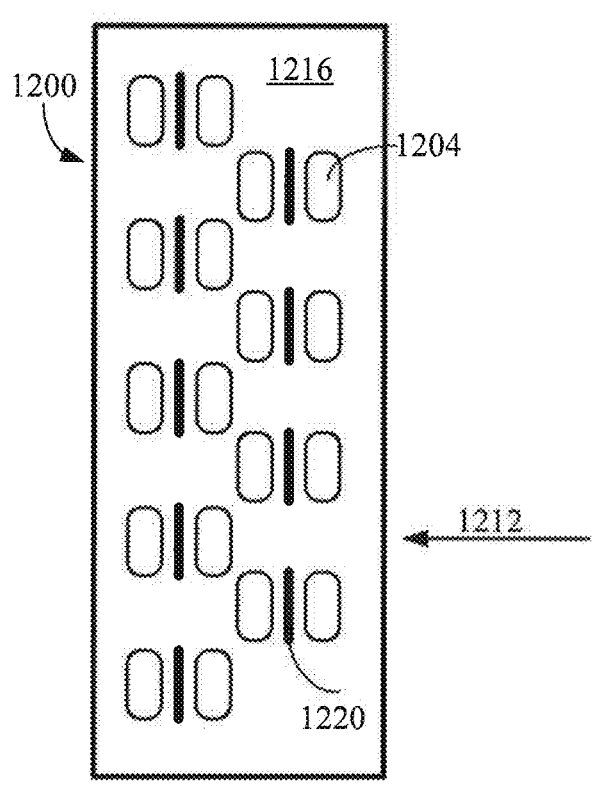
FIG. 12 is a schematic illustration of a two dimensional array of RF electrodes according to an example.

In one example, arrays 300, 600, 1000 and 1100 could be mechanically scanned or translated by displacing the array over the desired skin area. A two dimensional array 1200 (FIG. 12) of RF electrodes 1104 could be mechanically scanned/translated in a direction indicated by arrow 1212. The array 1200 of RF electrodes 1204 could be a plurality of staggered linear arrays shifted relative to each other such as when the array 1200 is translated over the skin it forms a continuous linear heated skin volume with temperature exceeding the surrounding skin temperature. Numeral 1220 schematically marks heated skin volumes located between pair of RF electrode 1204, where each RF electrode 1204 could further include a number of RF electrodes, for example two or three pairs of RF electrodes. Substrate 1116 on which electrodes 1104 are located could be a rigid or flexible substrate.

Electronic scanning has some advantages. Electronic scanning or switching of RF electrodes could support fast scanning of large skin segments. Since each electrode or pair of electrodes are individually and independently addressable, electronic scanning or switching of RF electrodes could also support simultaneous treatment of different skin segments with different RF voltage amplitude. In one example, substrate 1216 could be a flexible substrate e.g. silicone or plastic substrate populated by a two-dimensional array of RF electrodes 1204. The arrays of RF electrodes could be identical arrays located on a grid or staggered. Flexible substrate could be applied to different curved segments of the body and electronic switching of RF electrodes could support fast scanning of large and curved segments of the body. In order to ensure firm electrical contact between the RF electrodes and the subject skin, vacuum openings and channels could be included in a flexible substrate.

Flexible substrate could be applied to almost every segment of subject skin. It could be applied to limbs, thighs, love handles and others segments of the subject skin.

Further to this, the shift between active groups of electrodes could support scanning of different subject body segments at different depths. This could be easy achieved by changing the number of electrodes involved with each active group.

In all of the disclosed examples, RF electrodes are elongated electrodes with width to length ratio of at least 1:2 and all active RF electrodes switching methods are mutatis mutandis applicable to each and every example of RF electrodes arrays described above. Each and every example of RF electrodes arrays and/or substrates described above could include at least one sensor. The sensor could be of different types such as contact sensor, capacitive sensor, temperature sensor and other type of sensors as it could be desired by a particular skin treatment. Each of the sensors could communicate with RF voltage generator. The amplitude of the RF voltage supplied or applied to each pair of RF electrodes could be adjusted in response to at least one sensor.

Figure 13:
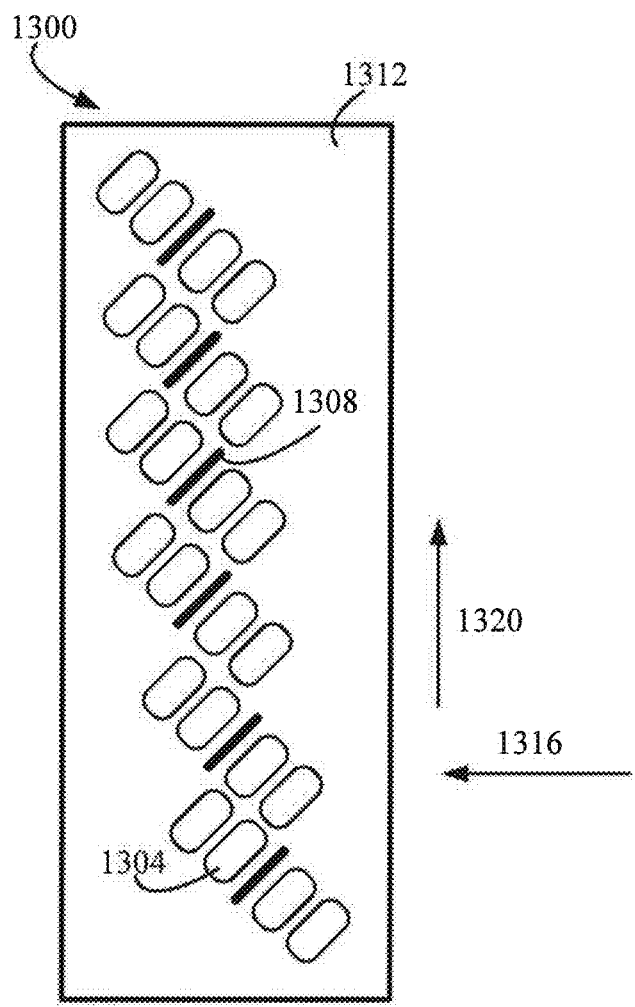
FIG. 13 is a schematic illustration of a two dimensional array of RF electrodes according to an additional example.

RF electrodes could be oriented in different direction and clusters of electrodes oriented in different directions could be combined on the same substrate. FIG. 13 is a schematic illustration of a two dimensional array of RF electrodes according to an additional example. Array 1300 includes a plurality of electrodes 1304 arranged in different configurations on substrate 1312. Numeral 1308 marks heated skin volumes. The temperature and depth and orientation in the skin of the heated volumes 1308 could be different. Array 1300 could be mechanically scanned in any one of directions 1316 or 1320.

In some examples additional energy sources like optical radiation sources being emitters of visible or non-visible optical radiation could be integrated in any one of the substrates described above. The same control unit could be configured to control each of the optical radiation sources including their timing and power.

In some examples a cooling arrangement including cold water circulation, cryogenic spray or thermoelectric Peltier unit could be integrated in any one of the substrates described above. The same control unit could be configured to control each of the cooling arrangements. A feedback provided by a temperature sensor could be used as an input to the control unit.

Knowledge of skin parameters and in particular of skin thickness, different skin layers electric conductivity, fat thickness could be of help in skin treatment. These and other skin parameters could be measured using the current system. A scanning linear array or a two dimensional array on a flexible substrate could be used for different skin parameters measurement and skin parameters map construction.

Electric impedance dependence on frequency from a wideband RF signal indicates different skin and fat parameters such as layer thicknesses and electric conductivity of the tissues. A wideband RF ramp signal including a large number of possible frequencies could be used for the electric impedance of skin and different skin layers determination. The wideband signal could be supplied as a) short pulse, i.e. having the duration smaller or of order of the central period; b) or sweep including a large number of frequencies.

What is claimed is:

1. A method for delivering energy to a target volume of skin comprising:
    contacting an area of skin covering a target volume by an applicator including a plurality of RF electrodes wherein the plurality of RF electrodes includes at least four RF electrodes arranged into an array with at least a pair of RF electrodes being an outer pair of RF electrodes and at least a pair of inner RF electrodes being separate and distinct from the outer pair of RF electrodes and nested between the outer pair of RF electrodes; and
    applying to each pair of the RF electrodes an RF voltage and wherein an amplitude of the RF voltage applied to the inner pair of RF electrodes is lower than an amplitude of the RF voltage applied to the outer pair of RF electrodes, so as to control a charge on each pair of the RF electrodes and thus control RF electric current streamlines allowing focusing of RF enemy in a specific region between the RF electrodes.

2. The method according to claim 1, wherein each pair of RF electrodes receives RF voltage from an autonomous RF voltage generator.

3. The method according to claim 1, wherein electric current streamlines produced by the RF voltage applied to the outer RF electrodes penetrate into the skin deeper than the electric current streamlines produced by the RF voltage applied to the inner RF electrodes.

4. The method according to claim 1, wherein electric current streamlines produced by the RF voltage applied to the outer RF electrodes limit penetration of the electric current streamlines produced by the inner RF electrodes.

5. The method according to claim 1, wherein electric current streamlines produced by the RF voltage applied to the outer and inner pair of electrodes heat a common skin volume located between the inner pair of electrodes.

6. The method according to claim 5, wherein the common skin volume located about the middle of the distance between the inner RF electrodes is located at least 1 micron below skin surface.

7. The method according to claim 1, wherein electric current streamlines produced by RF voltage applied to the most inner pair of electrodes are located closer to skin surface.

8. The method according to claim 1, wherein the array of RF electrodes is a two dimensional array of identical RF electrodes.

9. The method according to claim 1, wherein the RF voltage amplitude applied to each pair of electrodes is adjusted in response to at least one sensor.

10. The method according to claim 1, wherein electric currents induced by the RF voltage between different electrode pairs are equal.

11. The method according to claim 1, wherein a sum of currents flowing through all the RF electrodes is equal to zero.

12. The method according to claim 1, wherein the amplitude of the RF voltage supplied to each electrode is selected according to expression $$Vi \sim \{(1/\pi\sigma)[c_i \ln(d/4) + \Sigma c_j \ln|x_j - x_i|]\}$$

where:
Vi—is RF voltage amplitude supplied to the i-th electrode, with all voltage values being relative to a common reference point;
σ—is tissue conductivity (S/m);
$c_i/c_j$—is electric current flowing through a particular electrode;
d—is RF electrode width;
$x_j/x_i$—RF electrode center position;
i—index running from 1 to N;
j—index running from 1 to N except for i, i.e. j≠i;
$\Sigma c_j$—the sum of all $c_i$ must equal zero.

13. The method according to claim 1, wherein application of a vacuum supports firm electrical contact between the RF electrode and a subject's skin.

14. The method according to claim 5, wherein the common skin volume located between the inner pair of electrodes extends at least 1 micron below a surface of the skin.

15. The method according to claim 1, wherein control of the amplitude of the RF voltage signal supplied to different RF electrode pairs controls the RF voltage induced current streamlines supporting focusing of the RF energy in the specific region between the electrodes.

16. A method for delivering energy to a target volume of skin comprising:
- contacting an area of skin covering a target volume by an applicator including a plurality of RF electrodes wherein the plurality of RF electrodes includes at least four RF electrodes arranged into an array with at least a pair of RF electrodes being an outer pair of RF electrodes and at least a pair of inner RF electrodes being separate and distinct from the outer pair of RF electrodes and nested between the outer pair of RF electrodes; and
- applying to each pair of the RF electrodes an RF voltage and wherein an amplitude of the RF voltage applied to the inner pair of RF electrodes is lower than an amplitude of the RF voltage applied to the outer pair of RF electrodes, so as to control a charge on each pair of the RF electrodes and thus control RF electric current streamlines allowing focusing of RF energy in a specific region between the RF electrodes,
- wherein the array of RF electrodes is a plurality of staggered linear RF electrode arrays shifted relative to each other, and when the array is translated over the skin it forms a continuous linear volume with temperature exceeding surrounding skin temperature.

17. A system for aesthetic skin treatment comprising:
- an array of pairs of RF electrodes with at least a pair of inner RF electrodes nested between a separate and distinct pair of outer electrodes; and
- at least one RF voltage generator configured to selectively supply RF voltage to the inner and outer pairs of electrodes and wherein an amplitude of the RF voltage supplied to the pair of inner RF electrodes is lower than an amplitude of the RF voltage supplied to the pair of outer of electrodes, so as to control a charge on each pair of the RF electrodes and thus control RF electric current streamlines allowing focusing of RF energy in a specific region between the RF electrodes.

18. The system according to claim 17, wherein the at least one RF voltage generator is a single RF voltage generator through a bank of resistors that are selected to provide a desired RF voltage amplitude to each pair of electrodes.

19. The system according to claim 17, wherein the at least one RF voltage generator is a plurality of the RF voltage generators configured to provide RF voltage with a different amplitude to a predetermined pair of electrodes.

20. The system according to claim 19, wherein each of the plurality of the RF voltage generators is an autonomous RF voltage generator.

21. The system according to claim 17, wherein the outer RF electrodes pair are constructed and arranged to produce electric current streamlines that penetrate into skin deeper than electric current streamlines produced by the inner RF electrodes pair.

22. The system according to claim 17, wherein the system further includes a vacuum pump and wherein a flexible substrate includes channels and orifices communicating with the vacuum pump.

23. The system according to claim 17, wherein the array of electrodes is a plurality of staggered linear arrays shifted relative to each other such that when the array is translated over the skin it forms a continuous linear volume with a temperature exceeding surrounding skin temperature.

24. The system according to claim 17, wherein the array of RF electrodes is a two dimensional array of identical RF electrodes.

25. The system according to claim 17, wherein a flexible substrate includes at least one sensor selected from a group consisting at least of one of a temperature sensor, pressure sensor, and contact sensor.

26. The system according to claim 25, wherein the amplitude of the RF voltage applied to each pair of electrodes is adjusted in response to the at least one sensor.

27. The system according to claim 17, wherein the system further includes a scanning unit configured to translate a linear array across the skin.

28. The system according to claim 17, further comprising a control unit configured to control each of the plurality of RF voltage generators and wherein the control unit is a personal computer having a processor circuit.

29. The system according to claim 17, wherein to support focusing RF energy in a specific region between the electrodes, the at least one RF voltage generator controls the amplitude of the RF voltage signal supplied to different RF electrode pairs and accordingly controls the RF voltage induced current streamlines.

30. A method of skin and fat thickness and electric conductivity measurement comprising:
- contacting an area of skin by a plurality of electrodes wherein the plurality of electrodes includes at least four electrodes and wherein the electrodes are organized into an array with a first pair of electrodes flanking a second pair of electrodes, the second pair of electrodes being separate and distinct from the first pair of electrodes;
- applying to each pair of electrodes RF voltage and wherein an amplitude of the RF voltage applied to an inner pair of electrodes is lower than an amplitude of the RF voltage applied to an outer pair of electrodes, so as to control a charge on each pair of the RF electrodes and thus control RF electric current streamlines allowing focusing of RF energy in a specific region between the RF electrodes; and
- measuring an electric current induced by the RF voltage between each pair of electrodes;
- wherein the electric current between each pair of electrodes characterizes at least one skin parameter.

31. The method according to claim 30, wherein at least one skin parameter is a thickness of a skin layer through which measured electric current flows.

\* \* \* \* \*